United States Patent [19]

Greenfield

[11] 4,182,161
[45] Jan. 8, 1980

[54] APPARATUS FOR TIMING AND RECORDING SEDIMENTATION RATE OF FLUID SAMPLES

[76] Inventor: Walter Greenfield, 24 Eastern Dr., Ardsley, N.Y. 10502

[21] Appl. No.: 970,918

[22] Filed: Dec. 19, 1978

[51] Int. Cl.² .................................................. G01N 15/04
[52] U.S. Cl. ................................ 73/61.4; 346/33 ME; 356/39
[58] Field of Search ...................... 73/61.4; 356/39; 346/33 ME

[56] References Cited

U.S. PATENT DOCUMENTS

| | | | |
|---|---|---|---|
| 2,725,782 | 12/1955 | Worley | 73/61.4 X |
| 3,261,256 | 7/1966 | Morton, Jr. | 73/61.4 |
| 3,288,019 | 11/1966 | Blumenfeld | 73/61.4 X |
| 3,422,443 | 1/1969 | Jansen | 346/33 ME X |
| 3,474,458 | 10/1969 | Standaart | 356/39 X |
| 3,604,924 | 9/1971 | Standaart | 73/61.4 X |
| 3,952,579 | 4/1976 | Nakajima | 73/61.4 |

FOREIGN PATENT DOCUMENTS

| | | | |
|---|---|---|---|
| 2341403 | 2/1975 | Fed. Rep. of Germany | 73/61.4 |
| 2311304 | 12/1976 | France | 73/61.4 |

*Primary Examiner*—Gerald Goldberg
*Assistant Examiner*—Joseph W. Roskos
*Attorney, Agent, or Firm*—Edward H. Loveman

[57] ABSTRACT

A device for automatically timing and recording the sedimentation rate of fluid samples contained in cylindrical, transparent test tubes includes a generally rectangular rack having flat vertical walls formed with cylindrical bores for receiving the test tubes, and vertical channels at outer sides of the walls for receiving photographic strips. A lamp inside the rack shines through test tubes to the strips to record the amount of sedimentation of the fluid. The walls of the rack may be transparent for passing light therethrough or may be provided with slits at inner sides thereof for communicating with the bores. The bores communicate with the channels via other slits formed at outer sides of the bores. A rectangular housing may be fitted over the rack to exclude ambient light.

6 Claims, 8 Drawing Figures

APPARATUS FOR TIMING AND RECORDING SEDIMENTATION RATE OF FLUID SAMPLES

This invention relates to apparatus for timing and recording the sedimentation rate of fluid samples, and more particularly concerns an improved rack for holding a plurality of test tubes containing fluid samples, and an improved card including a plurality of photosensitive or photographic elements for recording sedimentation of samples in the rack.

In conventional devices for recording sedimentation of fluid samples, it is known to provide means for timing the vertical standing time of a mixture of a blood sample and anticoagulating chemical solution in a test tube and photographically recording the distribution of layers in the test tube at the completion of 60 minutes standing time. In the prior devices one or more test tubes are mounted in racks of various kinds. Individual photographic strips are placed adjacent the respective tubes in cartridges sealed by masking tape.

The present invention is directed at improvements in the rack and arrangement of the photographic strips. According to the invention, a rack is provided which holds a plurality of test tubes in vertical position arranged in groups of three. Each tube is placed in its own cylindrical compartment. The rack is rectangular in form and is made of transparent material so that light from a lamp inside the rack can shine through the tubes to photosensitive strips disposed in vertical channels at outer sides of the rack. The strips are arranged in cards of three strips to a card. The vertical channels have slits adjacent the photosensitive strips for passing light therethrough. A light-tight housing may be fitted over the rack to exclude ambient light. A timing circuit including time delay switches and a lamp is provided for energizing the lamp after the test tubes have been standing a predetermined time, 60 minutes for example, and for turning off the lamp after exposure of the samples to the photographic elements is completed.

It is therefore a principal object of the present invention to provide a device including a rack for supporting a plurality of transparent test tubes in vertical position surrounding a lamp, with a plurality of slits in walls of the rack to pass light therethrough, and with channels in the walls to support photographic strips adjacent to the test tubes.

A further object of the present invention is to provide a device as described, wherein the walls of the rack are transparent to pass light of the lamp therethrough.

Another object of the present invention is to provide a device as described, with an automatic timing circuit for the lamp.

Yet another object of the present invention is to provide a device as described, wherein the photographic strips are arranged in groups on cards.

Still another object of the present invention is to provide a device as described with an opaque box-like cover to enclose the rack and exclude ambient light.

These and other objects and many of the attendant advantages of this invention will be readily appreciated as the same becomes better understood by reference to the following detailed description when considered in connection with the accompanying drawings in which.

Figures 1, 2:
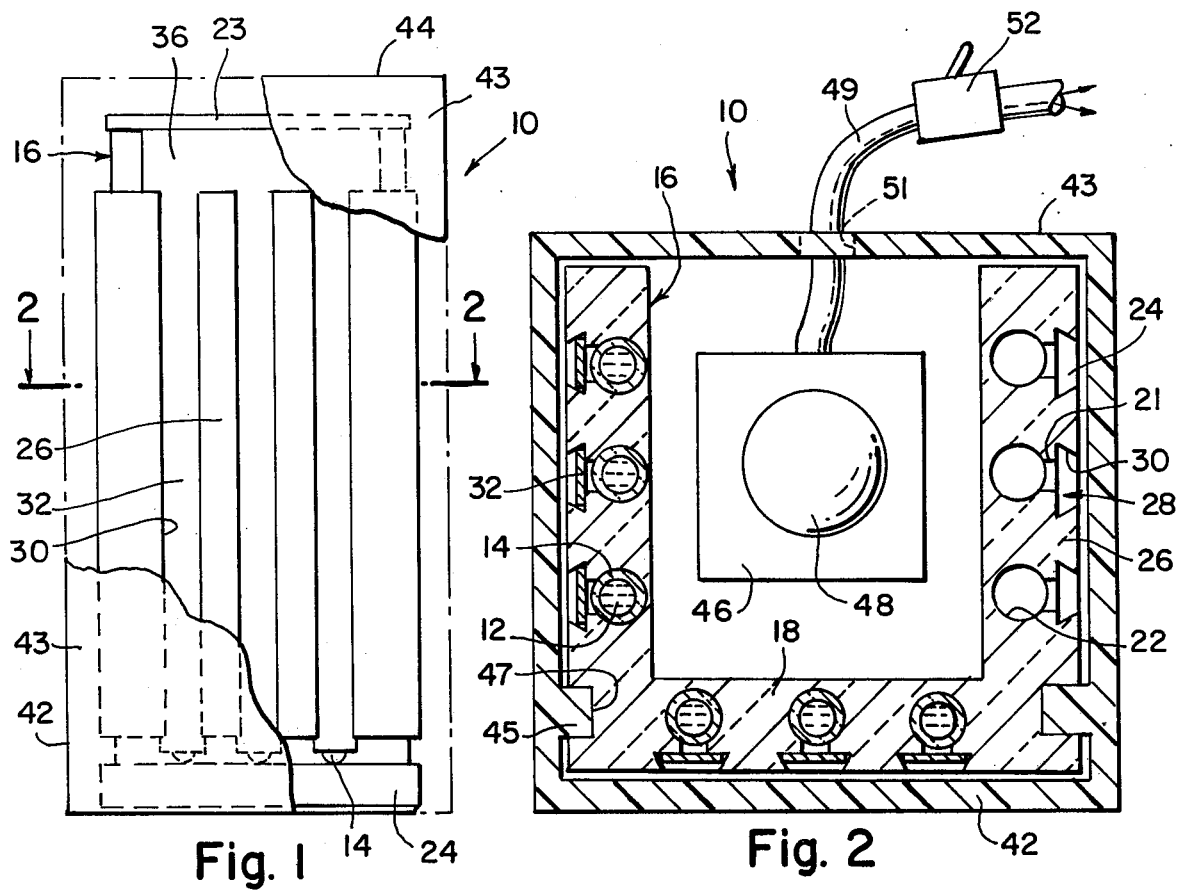
FIG. 1 is a front elevational view of a device for recording sedimentation rate of fluid samples in test tubes contained in a rack, parts of a removable cover are broken away.
FIG. 2 is an enlarged horizontal cross sectional view taken along line 2—2 of FIG. 1.
Figure 6:
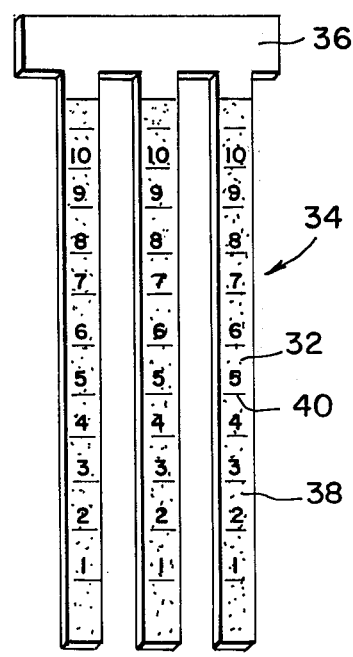
FIG. 6 is an oblique front and side view of a photographic card employed in the device.

Referring now to the drawings wherein like reference characters designate like or corresponding parts throughout, there is illustrated in FIGS. 1 and 2, a device generally designated as reference numeral 10 for recording the sedimentation rate of a fluid 12 in a test tube 14 mounted axially vertical in a rack 16. The rack 16 as shown in FIGS. 1–5 is a rectangular structure with three mutually perpendicular walls 18 formed as an integral unit from transparent plastic material. Each of the walls 18 contain three parallel, cylindrical bores 22, each just large enough in diameter to receive the test tube 14 and open to a vertical slit 21 which is, as long as, one of the test tubes 14. Each of the bores 22 is open at a top 23 and closed at a bottom 24. The rack 16 is arranged as a three sided structure open at the back as clearly shown in FIGS. 2 and 4, so that each side 18 is equally spaced from a lamp 48. Integrally formed with the outer sides of the walls 18 are four dovetailed ridges 26 defining four vertical channels 28 with inclined sides or edges 30 communicate with the slits 21 and the bores 22. The channels 28 snugly receive three strips 32 of a photographic card 34 best shown in FIG. 6. The card has an upper flat integral bridge 36 from which depend the three photographic strips 32. Each strip 32 is coated with a photosensitive film 38. Numbered lines or graduations 40 may be preprinted on the strips 32. The strips 32 may be inserted downwardly into the channels 28 until the bridge 36 rests on top of the rack wall 18. The rack 16 can hold three cards 34 at one time. Only two such cards are shown in FIG. 6.

A rectangular housing or cover 42 having a closed top 44 walls 43 and an open bottom may be placed vertically over the rack 16 to enclose it. Inside the walls 43 are ridges 45 which slide in mating grooves 47 formed in outer sides of the rack 16. Inside the rack 18 can be placed a circuit box 46 on which is the lamp 48. A power cord 49 extends outwardly of the assembly through a slot or hole 51 at the bottom of the wall 43 of the housing 42. A switch 52 may be provided on the power cord 49.

Figure 7:
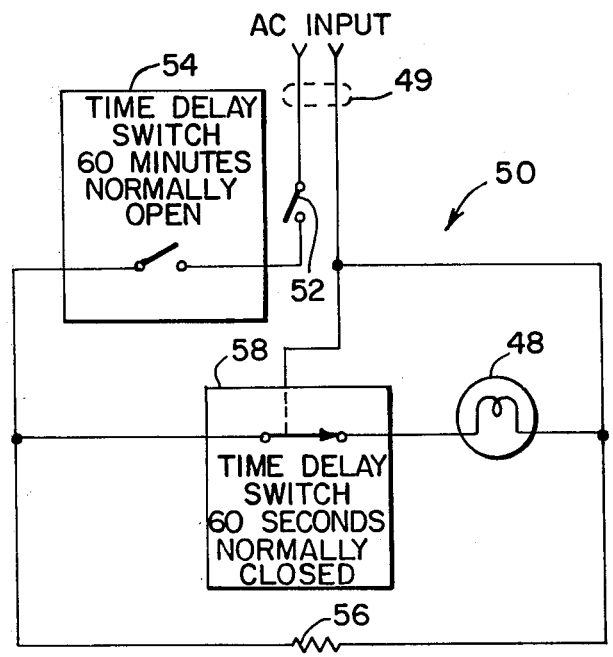
FIG. 7 is a diagram of the timing circuit for the lamp employed in the device.
Figure 3:
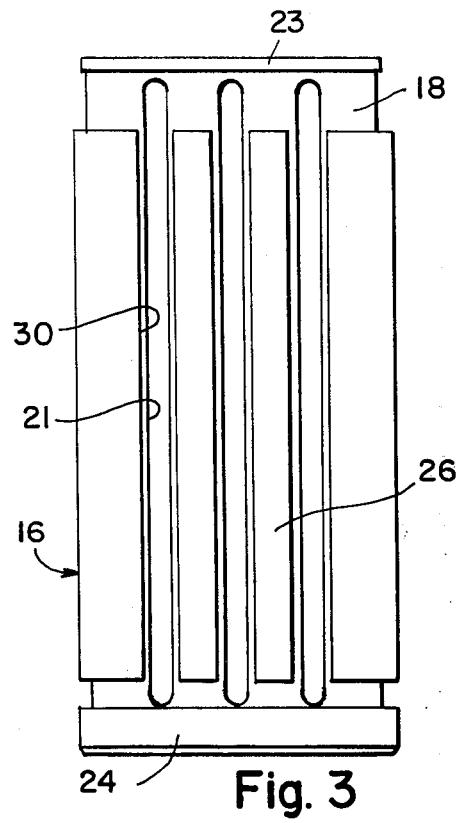
FIG. 3 is a front elevational view of the rack per se.
Figure 5:
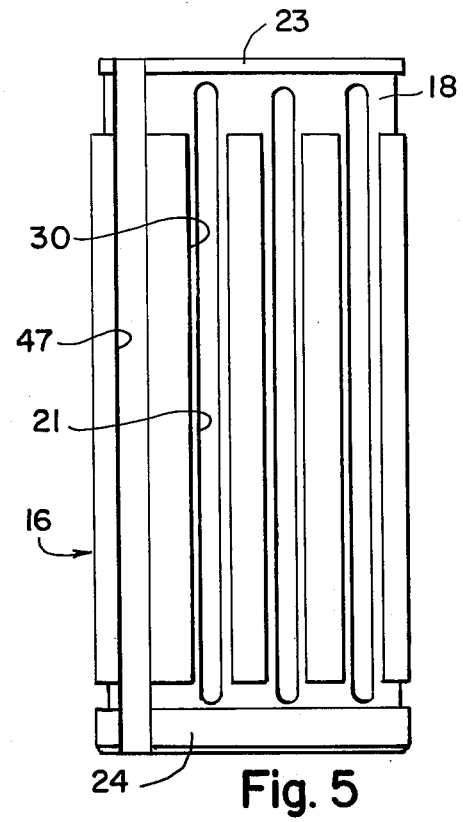
FIG. 5 is a side elevational view of the rack taken along line 5—5 of FIG. 4.
Figure 4:
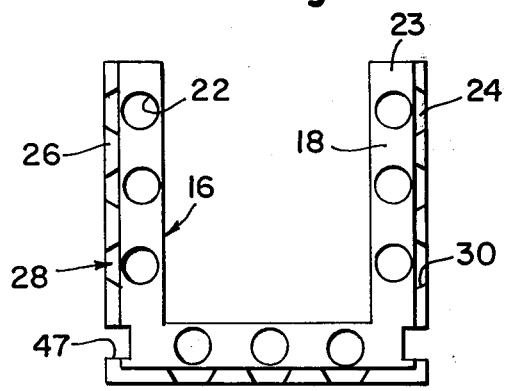
FIG. 4 is a top plan view of the rack of FIG. 3.

FIG. 7 shows a circuit 50 which may be used in the device 10. In this circuit a starting switch 52 is connected in a series circuit with the power line 49, with a normally open time delay switch 54 and a voltage dropping resistor 56. Connected across the line in series with the switch 54 is a normally closed time delay switch 58 and the lamp 48.

In operation of the device 10, plurality of test tubes, 14 containing blood samples are inserted in the bores 22. The lamp 48 is turned off. The housing 42 is placed over the rack 16. The switch 49 is manually closed to apply power to the switch 54. After a predetermined time, generally one hour, the switch 54 closes applying power to the lamp 48 which illuminates the photosensitive layers 38 via the transparent walls 18 of the rack 16, the transparent tubes 14, and the fluid 15. After a predetermined time, 60 seconds or less, the time delay switch 58 will open to turn off the lamp 48. The switch 52 may then be opened and reclosed to start another cycle.

After the cycle is completed, the housing 42 may be removed and the photographic cards may be removed. Since the strips are joined in groups of three, they can be easily handled.

Figure 2A:
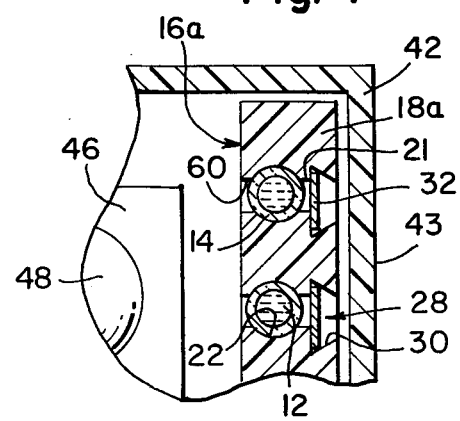
FIG. 2A is a fragmentary cross sectional view similar to a part of FIG. 2 illustrating a modification of the invention.

In FIG. 2A is illustrated a modification of the invention wherein the walls 18a of rack 16a are made of opaque plastic or other material. Further vertical slits 60 are provided at the inner sides of the walls 18 of the rack 16a communicating with the bores 22 to pass light from the lamp 48 through the transparent test tubes 14 in the bores 22 and via the slits 21 to the photographic strips 32 in the channels 28.

The device described is very light in weight, durable in construction, basically simple in structure, and relatively inexpensive to manufacture. The rack and housing can easily be sterilized. Although the rack 16 described hereinabove is rectangular in shape, it is obvious that the rack 16 may take other forms i.e. circular, semicircular, etc., as long as, the photographic cards on the rack 16 are equally spaced from the light 48.

It should be understood that the foregoing relates to only a limited number of preferred embodiments of the invention which have been by way of example only and that it is intended to cover all changes and modifications of the examples of the invention herein chosen for the purposes of the disclosure, which do not constitute departures from the spirit and scope of the invention.

The invention claimed is:

1. A device for automatically timing and photographically recording the sedimentation rate of a plurality of fluid samples contained in a corresponding plurality of cylindrical, transparent test tubes, comprising:
   a lamp,
   a plurality of photographic paper means,
   a rack having a vertical wall means surrounding said lamp, said wall means having;
   a plurality of vertical, cylindrical bores for receiving said tubes, each of said bores being substantially, equally spaced from said lamp;
   each of said vertical bores having a vertical slit adjacent to and opening into said bores respectively, the length of each of said vertical slits being substantially equal to the length of one of said test tubes;
   vertical channels adjacent to and opening into said slits for receiving said photographic paper means; and
   a rectangular box-like housing removably disposed over said rack to exclude ambient light therefrom.

2. A device as defined in claim 1, wherein said wall means of said rack are transparent to pass light from said lamp through said wall means for illuminating said photographic paper means.

3. A device as defined in claim 1, wherein said photographic means comprises a plurality of photographic cards, each of said card being narrow enough to fit into one of said channels and wide enough to fit snugly to exclude ambient light from passing through one of said channels.

4. A device as defined in claim 1, wherein said rack is generally "U" shaped with vertical wall integrally joined to form a unitary structure.

5. A device as defined in claim 4, further comprising time delay switches connected in circuit with said lamp and arranged to turn said lamp on predetermined time after a sedimentation timing cycle begins and to turn said lamp off a predetermined other time after said lamp is turned on.

6. A device as defined in claim 1, wherein said wall means of said rack are opaque and are formed with other vertical slits on inner sides thereof communicating with said bores for passing light from said lamp therethrough onto said photographic paper means.

* * * * *